United States Patent [19]

Marker et al.

[11] Patent Number: 5,243,102
[45] Date of Patent: Sep. 7, 1993

[54] ETHERIFICATION OF C$_5$-PLUS OLEFINS BY SEQUENTIAL CATALYTIC DISTILLATION

[75] Inventors: Terry L. Marker, Warrenville; Charles P. Luebke, Mt. Prospect, both of Ill.

[73] Assignee: UOP, Des Plaines, Ill.

[21] Appl. No.: 955,169

[22] Filed: Oct. 1, 1992

[51] Int. Cl.$^5$ .................. C07C 41/01; C07C 43/00
[52] U.S. Cl. ........................ 568/697; 568/698
[58] Field of Search ..................... 568/697, 698

[56] References Cited

U.S. PATENT DOCUMENTS

| 3,506,408 | 4/1970 | Kageyama et al. | 23/288 |
| 3,634,535 | 1/1972 | Haunschild | 260/677 A |
| 4,950,803 | 8/1990 | Smith, Jr. et al. | 568/697 |

FOREIGN PATENT DOCUMENTS

| 0078422 | 5/1983 | European Pat. Off. | 568/697 |
| 0129842 | 1/1985 | European Pat. Off. | 568/697 |
| 0390596 | 10/1990 | European Pat. Off. | 568/697 |
| 0451989A1 | 3/1991 | European Pat. Off. | |

Primary Examiner—Werren B. Lone
Attorney, Agent, or Firm—Thomas K. McBride; John F. Spears, Jr.

[57] ABSTRACT

Ethers suitable for use as high octane oxygenate additives for motor fuels are produced by a multistage catalytic distillation process wherein a multi-carbon number range olefin feed stream, e.g. C$_5$–C$_7$ isoolefins, is charged to two catalytic distillation zones operated in series. The heavier paraffins and olefins in the olefin feed stream and a first product ether are concentrated into the bottoms stream of the first catalytic distillation zone. This bottoms stream and additional alcohol is passed into the second catalytic distillation zone in which the heavier isoolefin is consumed in the production of a second ether. Preferably a portion of the catalytic distillation zone overhead liquid is passed into an external close coupled adiabatic reactor.

16 Claims, 1 Drawing Sheet

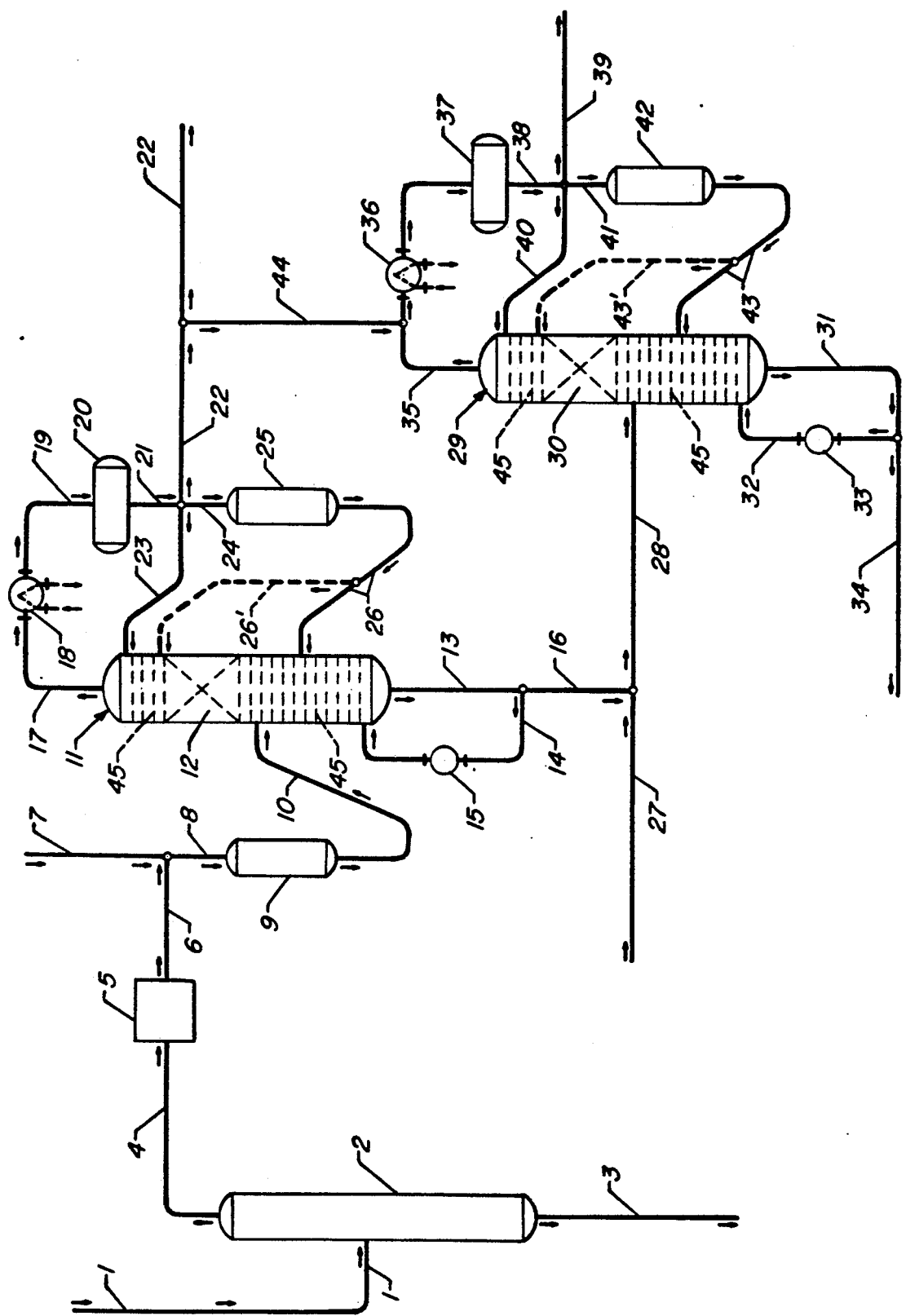

ETHERIFICATION OF C₅-PLUS OLEFINS BY SEQUENTIAL CATALYTIC DISTILLATION

FIELD OF THE INVENTION

The invention relates to a hydrocarbon conversion process useful in the etherification of isoolefins such as amylene and isohexylene (iso-1 hexene). The invention also relates to the use of catalytic distillation to perform hydrocarbon conversion reactions. The invention also specifically relates to a process wherein the isoolefins in a $C_5$-$C_6$ naphtha cut are reacted with methanol or higher alcohols to form an ether.

PRIOR ART

U.S. Pat. No. 3,506,408 to O. Kageyama et al. illustrates the use of catalytic distillation for carrying out reversible liquid phase reactions such as the production of acetals and esters by the reaction of two organic feed compounds. This reference teaches the use of ion exchange resin particles located on shelves with layers of packing such as Raschig rings located above the catalyst.

U.S. Pat. No. 3,634,535 to W. Haunschild and the references incorporated therein are pertinent for showing that ethers including methyl tertiary butyl ether (MTBE) can be produced by catalytic distillation (concurrent reaction and distillation) performed on distillation trays or with catalyst in the form of packing. Etherification by catalytic distillation is also described in U.S. Pat. No. 4,950,803 issued to L. A. Smith et al.

European Patent Application 0451 989 A1 by S. Mizrahl et al. discloses a multistep process wherein $C_5$-$C_8$ tertolefins in a naphtha fraction from an FCC unit are etherified.

BRIEF SUMMARY OF THE INVENTION

The invention is a hydrocarbon conversion process for the production of ethers which provides an increased yield of higher molecular weight ethers in a conventionally sized catalytic distillation column. The invention also achieves higher conversions when processing a mixture of higher olefins, such as isoamylene and isohexylene, than is provided by conventional catalytic distillation processes.

One broad embodiment of the invention may be characterized as a process for the production of ethers which comprises the steps of passing an alcohol and a hydrocarbon feed stream comprising a mixture of at least two different $C_5$-plus reactive isoolefins into a first catalytic distillation zone containing a central catalytic distillation section including a retained etherification catalyst, with the first catalytic distillation zone being operated under conditions which result in the reaction of the alcohol with a first $C_5$-plus tertiary isoolefin in the central catalytic distillation zone and the separation of compounds present in the first catalytic distillation zone into a first overhead stream, comprising the first $C_5$-plus isoolefin and the alcohol, and a first net bottoms stream, which comprises a first $C_6$-plus product ether, $C_6$ hydrocarbons from the feed stream and a second $C_5$-plus isoolefin; and passing an alcohol, which may be the first alcohol, and at least a portion of the first net bottoms stream into a second catalytic distillation zone containing a central catalytic distillation section including a retained etherification catalyst, with the second catalytic distillation zone being operated under conditions which result in the reaction of the alcohol with reactive $C_5$-plus tertiary olefins to form a second $C_6$-plus product ether and the separation of compounds present in the second catalytic distillation zone into a second overhead stream, comprising a $C_5$-plus isoolefin and the second alcohol, and a second net bottoms stream comprising the first and second $C_6$-plus product ethers and remaining unreactive hydrocarbons from the feed stream.

BRIEF DESCRIPTION OF THE DRAWING

The drawing is a simplified process flow diagram showing a naphtha splitter column 2, which prepares a $C_5$-$C_6$ feed stream for the sequential close-coupled catalytic distillation zones 11 and 29.

DETAILED DESCRIPTION AND PREFERRED EMBODIMENTS

The continuous quest for more economical processes for the production of petrochemicals is driving the development of etherification and alkylation processes employing "catalytic distillation". In these processes the conversion catalyst is retained within a structure or container capable of promoting vapor-liquid contact and fractional distillation. The catalyst is present in an overall apparatus which resembles a fractionation column. This apparatus is provided with means to effect reflux and reboiling and normally has vapor-liquid contacting devices, e.g., fractionation trays in both its upper and lower ends.

In the case of exothermic reactions such as alkylation, the heat released by the reaction is allowed to vaporize a portion of the reactants. This causes the more volatile reactants to pass upward through the overall apparatus while the less volatile reaction products flow downward in a liquid phase. This allows a facile method for separating the product from the reactants and controlling the temperature of the reactants. This fractionation within the reaction zone aids in product recovery but more importantly also tends to drive the desired reaction to completion by removing the product and supplying fresh reactants. A very high degree of conversion can therefore be achieved by employing catalytic distillation in suitable processes including etherification.

It was suggested in the past to apply catalytic distillation to a wide variety of processes such as butene isomerization (U.S. Pat. No. 2,403,672 to M. P. Matuzak); the hydrolysis of low molecular weight olefin oxides to produce mono-alkylene glycols (U.S. Pat. No. 2,839,588 to A. S. Parker); and the production of MTBE as described above. These early disclosures did not lead to commercialization. Catalytic distillation is only now emerging as a commercially viable hydrocarbon conversion and petrochemical processing tool.

It has recently been recognized that ethers formed from higher olefins, used herein to refer to $C_5$-plus, especially $C_6$-plus olefins, have very good octane numbers and are excellent gasoline blending components. This is set out in European Patent Application 0451 989 A1.

The etherification of nigher olefins occurs at a much slower rate than the etherification of low olefins such as isobutylene. This requires reactors used for the etherification of higher olefins to contain more catalyst. As a catalytic distillation zone should contain a large amount of open space for vapor and liquid flow to promote efficient distillation, the catalyst density in a catalytic distillation zone is much lower than a conventional "packed" bed of catalyst. The added structure required for catalytic distillation also increases the total cost per pound of installed catalyst. These effects combine to require quite large and expensive catalytic distillation reactors for etherifying $C_6$-plus olefins.

It is an objective of the subject invention to provide an improved process for the production of high molecular weight ethers by catalytic distillation. It is a further objective to reduce the size of the catalytic distillation process unit required for the etherification of heavy olefins such as $C_5$-$C_8$ olefins with isopropyl alcohol. It is also an objective of the invention to provide a higher overall conversion when processing mixtures of olefins such as $C_4$ and $C_5$ or $C_5$ and $C_6$ isoolefins.

These objectives are achieved by (1) employing "close-coupled" catalytic distillation reaction zones and (2) employing two or more catalytic distillation zones in series, with each zone directed to the etherification of a specific isoolefin. The "close coupled" catalytic distillation zones comprise a substantially adiabatic liquid phase (inlet) reactor tied directly to a conventional catalytic distillation zone and forming part of a recycle loop returning light reactants and some products to the catalytic distillation column, preferably below the base of the catalyst retaining mass in the catalytic distillation zone. This allows the process to increase the rate of ether production from an equal amount of catalytic distillation zone packing and to reduce the height and cost of the required overall apparatus.

The "close-coupled" nature of the two reaction zones is characterized by a small pressure drop between the reactor and the interior of the catalytic distillation zone of less than about 10 psia (69 kPa). A further evidence of this condition would be the absence of any pressure or flow control valve between the exit of the liquid-phase reactor and the interior of the catalytic distillation zone. The reactants charged to the top of the liquid-phase reaction zone are preferably restrained only by the inherent pressure drop of the closely packed catalyst employed in this zone and the associated conduits. The reactants, which preferably are slightly pressurized by a pump located in the overhead system, enter the upper end of the liquid-phase reactor at a pressure about 34–103 kPa (5–15 psia) above that present in the catalytic distillation zone. The temperature at the inlet of the reactor 25 is closely controlled to maintain liquid phase conditions at the inlet to the reactor.

The etherification reaction is quite exothermic. The reactor 25 is operated in a substantially adiabatic condition and therefore the reactants are heated as they pass downward through the reaction zone. This is employed beneficially in the subject process as the heat of reaction is useful in promoting the partial vaporization of the material flowing into the catalytic distillation zone and minimizes any disruption in the temperature profile of the catalytic distillation zone with no or minimal external heat exchange.

The majority of the discussion herein is directed to the preferred embodiment of higher olefin etherification. However, as those skilled in the art will recognize the invention is not so limited. The process of the subject invention can be applied in general to any reaction which is amendable to catalytic distillation and which is plagued by a slow reaction rate or other causes of low conversion. The undesired slow reaction rate can be attributable to the rate of reaction itself or to another closely related factor such as a diffusional resistance which limits the rate of reaction. A prime example of this is the hydration of olefinic hydrocarbons which is believed to be controlled to a great extent by the low mutual solubilities of the hydrocarbon and water phases.

The Drawing illustrates one nonlimiting embodiment of the invention. Referring now to the Drawing, a process stream comprising an FCC naphtha is passed into the fractionation column 2 through line 1. Column 2 is operated at conditions effective to divide this naphtha into an overhead stream comprising a substantially benzene free $C_5$-$C_6$ fraction carried by line 4 and a bottoms fraction carried by line 3 and comprising the benzene and higher boiling components of the naphtha of line 1. This light naphtha stream is preferably passed through a treating zone 5 wherein compounds detrimental to the downstream etherification catalyst are removed by adsorption or catalytic conversion to acceptable compounds. A preferred treatment is the selective hydrogenation of diolefinic hydrocarbons to mono olefinic hydrocarbons. The stream of line 4 should also be treated to reduce sulfur compounds to a low level if this has not been done upstream.

The light naphtha effluent of the treating zone 5 is removed through line 6 and admixed with a methanol feed stream carried by line 7. This admixture of $C_5$ and $C_6$ olefins and paraffins and methanol is passed through line 8 into a fixed bed liquid phase reaction zone 9. The contacting of the isoolefins and methanol of line 8 with the catalyst present in this reaction zone at etherification conditions results in the reaction of some of the $C_5$ and $C_6$ iso olefins and the production of some of the desired product ethers. The reaction zone effluent stream is passed through line 10 into a first catalytic distillation zone 11. The ethers formed in the reaction zone 9 and $C_6$ hydrocarbons present in the light naphtha of line 4 descend to the bottom of the column. The lighter components of the streams carried by lines 10 and 26 rise upward through the catalytic distillation column 11 and ascend into the intermediate zone of this apparatus containing the etherification catalyst zone 12. While in contact with the catalyst, additional quantities of methanol and the tertiary hexylene react to form additional amounts of the tertiary hexyl methyl ether.

Fractionation of the various compounds occurs within this packed catalyst retaining zone 12 resulting in the product ether descending downward. Unreacted feed methanol and $C_5$ olefins and paraffins continue to rise upward through the overall apparatus at the conditions which are preferred for its operation. The material exiting the top of the catalyst retaining zone will contain an admixture of all three basic components, the alcohol, olefin and product ether(s) together with any $C_5$-minus paraffins present in the feed to the catalytic distillation zone. The fractionation trays 45 or other fractional distillation material such as packing located in the top section of catalytic distillation column 11 perform an additional separation as required to remove essentially all of the product ether from the vapor phase material which is then withdrawn from the top of the zone 11 via line 17. The overhead vapor stream of line 17 should therefore be essentially free of the product ether but will contain inert materials, such as $C_5$ paraffins, present in the feedstream which pass through the reaction zone and are not converted therein. These inert materials together with the methanol and remaining $C_5$ olefins are condensed in the overhead condenser 18 and carried by line 19 as liquid phase overhead material collected in the overhead receiver 20.

A stream of liquid phase overhead material is removed through line 21 and divided into a first portion returned to the upper end of the catalytic distillation zone 11 through line 23 as reflux. A second portion of the overhead liquid of line 21 is removed through line 22 as a net overhead product removed as a drag stream for the purpose of eliminating from the process any paraffinic hydrocarbons present in the feedstream of line 10.

A third portion of the overhead liquid is diverted through line 24 and warmed in a heat exchanger not shown to a desired etherification temperature. This stream, which is at a higher pressure than the catalytic distillation column 11 due to passage through a pump not shown on the Drawing, is fed into an upper end of packed etherification reactor 25. This highly adiabatic close-coupled reactor contains a bed of solid resin catalyst. The feed enters at liquid phase conditions. The contacting of the methanol and olefinic hydrocarbons present in the overhead liquid with the catalyst results in an additional amount of the desired product tertiary hexyl methyl ether being formed. The effluent of the reactor 25 is removed via line 26 and passed directly into the catalytic distillation column 11. Preferably, this is done at a point below the catalyst zone 12, but a portion or all of the effluent of the reactor 20 may be passed via line 26' into the catalytic distillation column 11 at points above or at the same level as the etherification catalyst. In this manner, the unreacted feed components present in the overhead liquid are brought down to a lower point in the apparatus and exposed to a larger quantity of catalyst. This also allows the repeated upward passage of the methanol as vapor. The point of liquid return or the split will be governed largely by the kinetics of the ether formation and breakdown reactions. While it is normally desired to remove the ether product from contact with the catalyst, in some cases the rate of ether decomposition is slow enough that the benefits of returning the liquid at a higher point outweigh the losses due to ether decomposition.

A bottoms stream comprising the less volatile components of the stream carried by line 10 and the ethers produced in zones 9 and 11 is removed via line 13. In a customary manner a portion of the bottoms stream is diverted through line 14 and reboiler 15 to supply heat and vapor to the bottom of the column. The remaining net bottoms stream continues through line 16 and is admixed with additional methanol from line 27 before being passed into a second catalytic distillation zone 29 through line 28. This second zone functions in a manner very similar to the first zone 11, with the exception that the heavier $C_6$ olefins are driven upward into the catalyst retention zone 30. $C_7$ ethers formed in the catalyst zone pass downward through the catalyst retaining-packing and trays 45. The overhead vapor removed in line 35 will contain unreacted methanol and $C_6$ olefins and paraffins. The overhead vapor is condensed in the overhead condenser 36 and collected in the receiver 37. The overhead liquid stream of line 38 is divided into the reflux stream of line 40, a net overhead stream of line 39 and a third stream passed into adiabatic reactor 42 through line 41.

The process stream of line 41 is preferably heated and pressurized by means not shown to bring the reactants up to a desired etherification temperature and to ensure liquid phase conditions at the inlet to the adiabatic reactor 42, which is close coupled to zone 11. The effluent of the reactor is allowed to flash directly into the catalytic distillation zone 11 through line 43. A portion of the effluent of reactor may be passed into the catalytic distillation zone through line 43'. A bottoms stream comprising the product ethers is removed via line 31. By proper selection of fractionation conditions and equipment the bottoms stream can be essentially free of $C_5$ and/or $C_6$ hydrocarbons. These hydrocarbons would be removed as part of the net overhead stream of line 39. The net overhead streams of lines 22 and 39 are preferably passed into an alcohol recovery zone such as a water wash column and then sent to further process units or employed as motor fuel components. A portion of the bottoms stream is diverted through line 32 and reboiler 33 to provide vapor and heat for distillation within zone 29 and the remainder of the bottoms liquid is removed as a ether product stream via line 34.

The process described above is subject to considerable variation. For instance, the fractionation conditions employed in zone 29 can be adjusted such that the product stream of line 34 will contain significant amounts of $C_6$ hydrocarbons in addition to the ethers. A further variation is the heat and flow integration provided by passing all or a portion of the net overhead liquid of line 22 through line 44 into line 35. This allows at least a partial condensation of the overhead vapor of zone 29 by direct heat exchange. It also recycles the methanol in the stream of line 22 into a reaction zone. The amount of any recycling through lines 24, 44 and 41 is limited by the necessity of removing unreactive paraffins and olefins from the system to control the size of the required vessels and lines, etc.

There are other possible variations to the process embodiment shown in the Drawing. For instance the feed streams of line 10 and 26 may be admixed before being charged to the catalytic reaction zone and the preliminary reactor 9 could be deleted. An internal overhead condenser can be employed instead of an external condenser. Other possible variations relate to the construction of the vapor-liquid contacting devices employed in the process. The Drawing illustrates the use of fractionation trays. These may be any type of tray with a sieve tray having a conventional downcomer arrangement being suitable. Another suitable type of fractionation tray is referred to as a Multiple Downcomer tray. This type of tray is described in U.S. Pat. No. 3,410,540. Those portions of the overall vessel devoted to fractionation can alternatively contain structured or dumped packing material and suitable liquid distributors.

The etherification embodiment of the subject process consumes two different reactants. The first is a $C_5$-$C_8$ tertiary olefin such as an amylene ($C_5H_{10}$), hexylene ($C_6H_{12}$), heptylene or octylene ($C_8H_{16}$). It is contemplated that in the normal commercial application of the subject process these olefinic reactants, which are branched at the double bond, will be present in a mixture of other nonreactive branched and straight chain olefinic hydrocarbons having the same number of carbon atoms per molecule. Therefore, a preferred feed olefin, such as isohexylene, will normally be present in the feed stream in admixture with one or more hexylene isomers. The expected hydrocarbon feed streams to the subject process will be derived from a fluid catalytic cracking (FCC) reaction zone, a thermal cracker or similar large scale refining process and are expected to contain a mixture of all of the possible olefin and paraffin isomers in an approximate equilibrium concentration. Part or all of the olefin feed stream also could be derived from the effluent of a dehydrogenation process. The hydrocarbon feed to the process is preferably fractionated to contain only molecules having a two or three carbon number range. The feed stream may therefore be a $C_5$-$C_6$ fraction, a $C_5$-$C_7$ fraction, a $C_6$-$C_7$ fraction, etc. It is preferred that a separate catalytic distillation zone is used for each carbon number olefin, e.g., three reaction zones with a $C_5$-$C_7$ feed. The olefin-containing feed stream can be purified by adsorptive separation to yield a high purity olefin feed stream which is charged to the process.

The second reactant consumed in the etherification embodiment of the process is a $C_1$-$C_4$ acyclic alcohol such as methanol, ethanol, propanol or butanol. The product hydrocarbon can therefore be one of a wide variety of $C_6$-$C_{12}$ ethers including tertiary amyl methyl ether(TAME), tertiary- amyl ethyl ether, tertiary-amyl propyl ether. tertiary-amyl n-butyl ether, methyltertiary hexyl ether and methyl tertiary heptyl ether. The preferred reactants are an amylene with methanol, ethanol or isopropanol and a hexylene with methanol, ethanol or isopropanol.

The same or different alcohol(s) may be used in the different reaction zones. In one embodiment of the invention a lighter (lower carbon number) alcohol is consumed in the second catalytic distillation zone as compared to the first catalytic distillation zone. For instance, a $C_5$ olefin is reacted with ethanol in the first zone and a $C_6$ olefin is reacted with methanol in the second zone. Both zones may therefore produce $C_7$ or $C_8$ ethers. While the ethers will be different, they will be similar in physical characteristics such as boiling point and volatility, facilitating their recovery in common product recovery systems.

While some of the higher boiling ethers resulting from the reaction of these reactants may not be suitable for use in gasoline, they may be useful in diesel fuel, jet fuel or other fuels or as feed stocks in petrochemical processes or as end product petrochemicals having their own utility, such as solvents.

The subject process can be practiced with any suitable catalysts. This may be any heterogeneous catalyst which gives satisfactory performance in terms of conversion and selectivity for the desired reaction at the conditions required to allow fractional distillation of the reactants and products. The best catalysts to employ in the subject process will of course to a great extent depend upon the identity of the specific reactants to be converted in the process. It is contemplated that different catalysts can be employed in the catalytic distillation reaction zone and in the close-coupled liquid-phase reaction zone.

The preferred etherification catalyst is a macroporous acid form sulfonic ion exchange resin such as the sulfonated styrene-divinylbenzene resin as described in U.S. Pat. No. 2,922,822 having a degree of crosslinking of from about 5 to 60%. Suitable resins are available commercially. Specialized resins have been described in the art including copolymers of sulfonyl fluorovinyl ether and fluorocarbons as described in U.S. Pat. Nos. 3,784,399 and 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2$/g, a pore volume of 0.6-2.5 ml/g and a mean pore diameter of 40-1000 angstroms. A particularly suitable and preferred catalyst is sold under the designations Amberlyst 15 and 35 by Rohm & Haas.

It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Other catalysts which can be utilized in the process include zeolitic catalysts comprising beta zeolite or Y zeolite.

Various etherification process techniques, reaction conditions and product recovery methods are described in U.S. Pat. No. 4,219,678 to Obenous et al. and U.S. Pat. No. 4,282,389 to Droste et al. which are incorporated herein for this teaching.

The preferred apparatus for retaining the catalyst in the catalytic distillation zones is described in detail in U.S. Pat. No. 5,073,236 to A. P. Gelbein which is incorporated herein by reference for its teaching as to the structure and usage of these catalyst packing systems. These devices provide a means to evenly distribute the catalyst and reactants uniformly within the desired locations in the overall vessel. The apparatus is also very effective at promoting vapor-liquid contacting and therefore fractional distillation of the product(s) from the reactants.

While a structured catalyst retention device resembling structured column packing is preferred, there are other methods of retaining catalyst within the column which should also prove effective. For instance it is known that the catalyst may be retained upon the surface of perforated or sieve trays by the use of screens or bags or other particle retention means. It is also known that catalyst may be retained within downcomers used to convey liquid between fractionation trays.

Temperatures which are suitable for use in the subject process are similar to those employed in a conventional etherification process. The combination of temperature and pressure must be selected to maintain only a portion of the compounds in the catalytic distillation zones present as liquids since the etherification reaction is a liquid phase reaction while vapor is needed for distillation. Vapor is desired only as necessary to effect distillation. Suitable temperatures are from about 30° to about 140° C., especially from about 50° to about 100° C. Pressures which are suitable for use herein preferably are above about 1 atmosphere but should not be in excess of about 130 atmospheres. Desirable pressure range is from about 1.5 to about 30 atmospheres. The concept of space velocity does not apply to catalytic distillation. The reactants should be fed to the vessel in the proper stoichiometric ratio at a rate equal to their rate of consumption therein, which is most easily measured by monitoring the rate of ether production.

In accordance with above description one embodiment of the invention may be characterized as a process for the production of ethers which comprises the steps of forming a first process stream comprising an admixture of $C_5$-$C_6$ hydrocarbons including paraffins and isoolefins; passing a first alcohol and said first process stream into a first catalytic distillation zone containing a central catalytic distillation section including a retained etherification catalyst, with the first catalytic distillation zone being operated under conditions which result in the reaction of the first alcohol with $C_5$ tertiary olefins and the separation of compounds present in the first catalytic distillation zone into a first overhead stream, comprising unreacted $C_5$-plus isoolefins and the first alcohol, and a first net bottoms stream, which comprises a product $C_6$-plus ether and $C_6$ paraffins and isoolefins; and passing a second alcohol and at least a portion of the first net bottoms stream into a second catalytic distillation zone containing a central catalytic distillation section including a retained etherification catalyst, with the second catalytic distillation zone being operated under conditions which result in the reaction of the second alcohol with $C_6$ tertiary olefins to form a $C_7$-plus product ether and the separation of compounds present in the second catalytic distillation zone into a second overhead stream, comprising unreacted $C_6$-plus isoolefins and the second alcohol, and a second net bottoms stream comprising the $C_6$-plus and $C_7$-plus product ethers.

The liquid phase reaction zone(s) used in the close coupled catalytic reaction zones are preferably maintained at an inlet temperature of 35°–100° C. and a pressure sufficient to maintain liquid phase conditions at the reactor inlet. A pressure of from 1.2 to 20 atmospheres is preferred.

The operation of the subject invention may be illustrated by the following example which is based upon an engineering design. The combined feedstream of line 8 would contain approximately 540 lb moles per hour methanol and 1677 lb moles per hour of a mixed paraffin-olefin $C_5$-$C_6$ stream. This feed admixture would be contacted with an initial bed of resin-type catalyst present in a quantity of approximately 70 cubic meters in etherification reactor 9 and maintained at a pressure of 135 psia (931 kpa) at 40°–80 degrees Centigrade. The effluent stream of this reaction zone would be depressured to approximately 52 psia (358 kpa) and passed into the catalytic distillation zone 11. This zone comprises a column containing about 30 sieve trays in the lower portion of the column and about 15 sieve trays in the upper portion of the column. The stream of line 10 would enter three trays below the structured catalyst packing 12. The preferred structural packing referred to above would be present in the intermediate portion of the column. This portion of the column would contain approximately 42 cubic meters of the catalyst-containing packing material. The catalytic distillation column would be operated to maintain a temperature of approximately 68 degrees Centigrade and 50 psia (345 kpa), with these conditions being measured at a central location within the catalyst retention media 12. $C_6$ hydrocarbons and the ether formed in reactor 9 are concentrated into the bottoms stream of line 13 and do not enter the catalyst 12. The overhead stream of line 17 would have a flow rate of approximately 144,540 kg per hour and would be cooled to a temperature of approximately 50 degrees Centigrade in the overhead condenser 18 to effect its condensation. Approximately 48,180 kilogram per hour of this material would be passed to the upper portion of column 11 as reflux. A portion of the overhead liquid equal to about 28908 kg per hour would be withdrawn as the dragstream or net overhead product through line 22 with the remainder of this material being passed through line 24 into the close coupled side reactor 25. The closed coupled side reactor would be operated at an inlet pressure of about 56 psia (386 kpa) and an inlet temperature of about 45 degrees Centigrade. The effluent of this close coupled reactor 25 is expected to have a temperature of approximately 50 degrees Centigrade and contain 714 kg/hr of tertiary amyl methyl ether (TAME). The net overhead liquid stream of line 22 will have a concentration of approximately 11 wt. percent methanol and 89 percent $C_5$ olefins and paraffins. This net overhead stream may be passed to a waterwash column or other appropriate systems for the recovery of the methanol. The net bottoms stream of line 16 will contain approximately 11,550 kilograms per hour of tertiary amyl methyl ether (TAME) and 3,623 kg/hr of THME.

The net bottoms stream of line 16 is then admixed with a second methanol feed stream of line 27 and passed into the second catalytic distillation column 29. This combined feed stream enters 8 trays below the catalyst-retaining section 30, which consists of approximately 73 m$^3$ of the preferred structured packing with enclosed resin catalyst. The conditions used in this section include a pressure of about 22 psia (152 kPa) and temperature of about 68° C. The feed alcohol and reactive $C_6$ olefin(s) in the bottoms stream 13 react in this section to form a second product ether which is concentrated into the net bottoms (product) stream of line 34. This bottoms stream will contain about 11,550 kg/hr of TAME and 7,758 kg/hr of THME.

The overhead vapor stream of line 35 passes through the overhead condenser 36, with the condenser effluent being at approximately 16 psia (110 kPa) and 46° C. The condensate collected in receiver 37 is withdrawn via line 38 and divided into a net overhead stream of line 39 having a flow rate of about 20,676 kg/hr, a reflux stream of line 40 having a flow rate of about 51,690 kg/hr and a third stream of 65,476 kg/hr which is charged to the close-coupled adiabatic reactor 42 via line 41. The product from the close-coupled reactor contains about 2089 kg/hr of THME which is reintroduced via line 43 into the catalytic distillation unit 29 five trays below the catalyst section 30.

As mentioned above, the subject process can be used to perform reactions other than etherification. These reactions include esterification and olefin hydration reactions. Of these two reactions, hydration to produce alcohols suitable for use in motor fuels is believed the most desirable.

The hydration of olefinic hydrocarbons can be performed in a catalytic distillation column at known conditions using conventional acidic resin catalysts. Hydration conditions in general would include a temperature of from 60 degrees to 150 degrees Centigrade and a pressure of from about 200 to 500 psia (1380–3450 kPa). In general the hydration conditions are quite similar to those employed in etherification. The hydration and etherification of olefins to produce motor fuel blending components is described in U.S. Pat. Nos. 4,886,918 and 4,935,552 and in European Patent Application 0451989A1 which are incorporated herein by reference.

The preferred conditions for hydration of olefins normally include a higher pressure than employed for etherification. However, the reaction merely slows down at lower pressures and it is therefore feasible to perform some intentional olefin hydration simultaneously with the etherification reaction. This is especially true in the hydration of higher olefins such as the amylenes and hexylenes for two reasons. First the alcohols, such as tert amyl alcohol, have superior octane numbers compared to the lower alcohols. Second, the higher alcohols have a lower solubility in water which makes them easier to recover in the process and is also a desirable trait for a gasoline blending component.

One embodiment of the subject invention is therefore a process for the hydration of olefinic hydrocarbons to form a corresponding alcohol. Water would therefore be charged to the process as a feed compound. Examples of the alcohols which could be produced include isopropyl alcohol, tertiary butyl alcohol, tertiary amyl alcohol and tertiary hexyl alcohol. The process of the subject invention can also be employed in a process wherein both ethers and alcohols are produced simultaneously or in a process for the sequential production of an alcohol followed by its conversion to an ether. It is therefore contemplated that diisopropylether could be produced by first hydrating propylene and then reacting the resultant isopropyl alcohol with additional propylene.

The preferred method of performing olefin hydration in the subject process comprises feeding water at a low rate, equal to from 1 to 5 mole percent of the olefins in the hydrocarbon feed stream(s), into the catalytic distillation zone.

What is claimed:

1. A process for the production of ethers which comprises the steps:
   a. passing a $C_1$–$C_4$ alcohol and a feed stream comprising a mixture of two different $C_5$-plus reactive isoolefins into a first catalytic distillation zone containing a central catalytic distillation section including a retained etherification catalyst, with the first catalytic distillation zone being operated under conditions including a temperature from about 30° to about 140° C. and a pressure of about 1.5 to 30 atmospheres, which conditions result in the reaction of the alcohol with a first $C_5$-plus isoolefin and the separation of compounds present in the first catalytic distillation zone into a first overhead stream, comprising the first $C_5$-plus isoolefin and the alcohol, and a first net bottoms stream, which comprises a first $C_6$-plus product ether and a second $C_5$-plus isoolefin; and
   b. passing an alcohol and at least a portion of the first net bottoms stream into a second catalytic distillation zone containing a central catalytic distillation section including a retained etherification catalyst, with the second catalytic distillation zone being operated under conditions including a temperature from about 30° to about 140° C. and a pressure of about 1.5 to 30 atmospheres, which conditions result in the reaction of the alcohol with the second $C_5$-plus isoolefins to form a second $C_6$-plus product ether and the separation of compounds present in the second catalytic distillation zone into a second overhead stream, comprising the second $C_5$-plus isoolefin and the alcohol, and a second net bottoms stream comprising the first and second $C_6$-plus product ethers.

2. The process of claim 1 further characterized in that the alcohol passed into the first and second catalytic distillation zones is methanol.

3. The process of claim 1 further characterized in that at least one of the catalytic distillation zones is a close-coupled catalytic distillation zone having an external adiabatic etherification reactor.

4. The process of claim 3 further characterized in that the effluent of the adiabatic etherification reactor is passed into the catalytic distillation zone at a point below essentially all etherification catalyst located in the catalytic distillation zone.

5. The process of claim 1 wherein the second net bottoms stream comprises both tertiary amyl methyl ether and THME.

6. The process of claim 1 further characterized in that water is passed into a catalytic distillation zone and in that the second net bottoms stream comprises a $C_6$-plus alcohol formed by hydration of a feed olefinic hydrocarbon.

7. The process of claim 1 further characterized in that the alcohol passed into the first catalytic distillation zone contains one more carbon atom per molecule than the alcohol passed into the second catalytic distillation zone.

8. A process for the production of ethers which comprises the steps:
   a. forming a first process stream comprising an admixture of $C_5$–$C_6$ hydrocarbons including paraffins and isoolefins;
   b. passing a first $C_1$–$C_4$ alcohol and a said first process stream into a first catalytic distillation zone containing a central catalytic distillation section including a retained etherification catalyst, with the first catalytic distillation zone being operated under conditions including a temperature from about 30° to about 140° C. and a pressure of about 1.5 to 30 atmospheres, which conditions result in the reaction of the first alcohol with $C_5$ tertiary olefins and the separation of compounds present in the first catalytic distillation zone into a first overhead stream, comprising unreacted $C_5$-plus isoolefins and the first alcohol, and a first net bottoms stream, which comprises a product $C_6$-plus ether and $C_6$ paraffins and isoolefins,
   c. passing a second $C_1$–$C_4$ alcohol and the first net bottoms stream into a second catalytic distillation zone containing a central catalytic distillation section including a retained etherification catalyst, with the second catalytic distillation zone being operated under conditions including a temperature of about 50° to about 100° C. and a pressure of about 1.5 to 30 atmospheres, which conditions result in the reaction of the second alcohol with $C_6$ tertiary olefins to form a $C_7$-plus product ether and the separation of compounds present in the second catalytic distillation zone into a second overhead stream, comprising unreacted $C_6$-plus isoolefins and the second alcohol, and a second net bottoms stream comprising the $C_6$-plus and $C_7$-plus product ethers.

9. The process of claim 8 further characterized in that the first and the second alcohols are chosen from the group consisting of ethanol, methanol or isopropanol.

10. The process of claim 8 further characterized in that the catalytic distillation zones are close coupled catalytic distillation zones having an external adiabatic etherification zone.

11. The process of claim 10 further characterized in that the effluent of the adiabatic etherification zones is passed into the catalytic distillation zone at a point below essentially all etherification catalyst located in the catalytic distillation zone.

12. The process of claim 8 wherein the second net bottoms stream comprises both TAME and tertiary hexyl methyl ether.

13. The process of claim 8 further characterized in that water is passed into the first and/or second catalytic distillation zone and in that the second net bottoms stream comprises a $C_6$-plus alcohol formed by hydration of the feed olefinic hydrocarbon.

14. The process of claim 8 further characterized in that a portion of a liquid-phase overhead stream recovered from the first catalytic distillation zone is admixed with a vapor-phase overhead stream removed from the second catalytic distillation zone.

15. The process of claim 8 further characterized in that the first alcohol is ethanol and the second alcohol is methanol.

16. A process for the production of ethers which comprises the steps:
   a. passing a mixture of a $C_1$–$C_4$ alcohol and a mixture of at least two $C_5$-plus isoolefins through an etherification zone and forming a reaction zone effluent stream comprising a mixture of two ethers, the two $C_5$-plus isoolefins and the alcohol;
   b. passing the reaction zone effluent stream into a first catalytic distillation zone containing a central catalytic distillation section including a retained etherification catalyst, with the first catalytic distillation zone being operated under conditions including a temperature of about 50° to about 100° C. and a pressure of about 1.5 to 30 atmospheres, which conditions result in the reaction of the alcohol with $C_5$ tertiary olefins and the separation of compounds present in the first catalytic distillation zone into a first overhead stream, comprising an unreacted $C_5$-plus isoolefin and the alcohol, and a first net bottoms stream, which comprises a product $C_6$-plus ether and $C_6$ paraffins and isoolefins,
   c. passing an additional amount of a $C_1$–$C_4$ alcohol and the first net bottoms stream into a second catalytic distillation zone containing a central catalytic distillation section including a retained etherification catalyst, with the second catalytic distillation zone being operated under conditions including a temperature of about 50° to about 100° C. and a pressure of about 1.5 to 30 atmospheres, which conditions result in the reaction of the alcohol with $C_6$ tertiary olefins to form a $C_7$-plus product ether and the separation of compounds present in the second catalytic distillation zone into a second overhead stream, comprising an unreacted $C_6$-plus isoolefin and the alcohol, and a second net bottoms stream comprising the $C_6$-plus and $C_7$-plus product ethers; and,
   d. recovering the product ethers from the second net bottoms stream.

* * * * *